Figure 1:
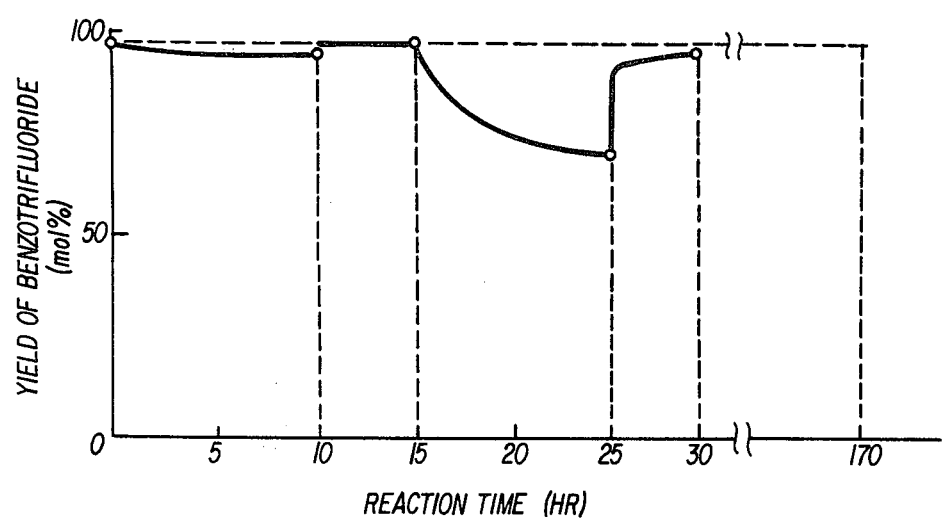

| United States Patent [19] | [11] | 4,242,286 |
|---|---|---|
| Ohsaka | [45] | Dec. 30, 1980 |

[54] PROCESS FOR PREPARING BENZOTRIFLUORIDE AND ITS DERIVATIVES

[75] Inventor: Yohnosuke Ohsaka, Takatsuki, Japan

[73] Assignee: Daikin Kogyo Co., Ltd., Osaka, Japan

[21] Appl. No.: 22,782

[22] Filed: Mar. 22, 1979

[30] Foreign Application Priority Data

Mar. 30, 1978 [JP] Japan .................................. 53-37681

[51] Int. Cl.³ ............................................. C07C 25/14
[52] U.S. Cl. ............................... 570/145; 260/465 G; 564/442; 568/936
[58] Field of Search ...................................... 260/651 F

[56] References Cited

U.S. PATENT DOCUMENTS

| 2,062,743 | 12/1936 | Daudt et al. .......................... 570/167 |
| 2,121,330 | 6/1938 | Scherer et al. ....................... 570/127 |
| 3,755,477 | 8/1973 | Firth et al. .......................... 260/653.4 |
| 3,950,445 | 4/1976 | Ryf ...................................... 260/651 F |
| 4,012,453 | 3/1977 | Nychka et al. ................... 260/649 F |
| 4,079,090 | 3/1978 | Buttner et al. ................... 260/651 F |

*Primary Examiner*—Curtis R. Davis
*Attorney, Agent, or Firm*—Stevens, Davis, Miller & Mosher

[57] ABSTRACT

A process for preparing bentotrifluoride or its derivatives by contacting benzotrichloride or its derivatives corresponding thereto with hydrogen fluoride in a gaseous phase, characterized in that the contact is carried out in the presence of aluminum fluoride and, if desired, of chlorine.

7 Claims, 1 Drawing Figure

PROCESS FOR PREPARING BENZOTRIFLUORIDE AND ITS DERIVATIVES

The present invention relates to a process for preparing benzotrifluoride and its derivatives. More particularly, it relates to an improved process for preparing benzotrifluoride or its derivatives by reaction of benzotrichloride or its derivatives corresponding thereto with hydrogen fluoride in a gaseous phase.

Benzotrifluoride and its derivatives are valuable intermediates for production of medicaments, dyestuffs, agricultural chemicals and the like and have been hitherto produced by reaction of benzotrichloride or its derivatives corresponding thereto with hydrogen fluoride in a heterogeneous liquid phase. For instance, benzotrifluoride is prepared in a liquid phase according to the following reaction:

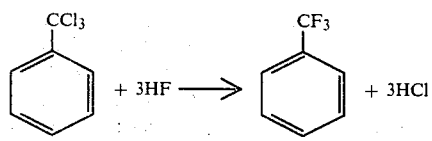

The said liquid phase reaction, however, has various drawbacks and disadvantages. Thus, the liquid phase reaction is generally carried out at a temperature of about 100° C. under a pressure of 20 to 40 Kg/cm$^2$G, which is a prerequisite to minimize any loss of hydrogen fluoride. Because hydrogen fluoride, as well as hydrogen chloride, is very dangerous, great care must be taken in effecting the reaction under such high pressure. In addition, there is required a considerable long period of time to complete the reaction because the reaction rate is extremely low in such liquid phase reaction. Furthermore, vigorous stirring under a high pressure and a high temperature is required because of the reaction in a heterogenous phase, and therefore an expensive high pressure reaction apparatus is needed.

As the result of an extensive research, it has now been found that the drawbacks and disadvantages as stated above can be overcome by effecting the reaction of benzotrichloride or its derivatives with hydrogen fluoride in a gaseous phase in the presence of aluminum fluoride as a catalyst.

Accordingly, the present invention provides a process for preparing benzotrifluoride or its derivatives which comprises contacting benzotrichloride or its derivatives corresponding thereto with hydrogen fluoride in a gaseous phase in the presence of aluminum fluoride.

The present invention has the following advantages: the loss of hydrogen fluoride can be minimized without applying a high pressure; owing to the high reaction rate, the capacity of the reaction apparatus may be reduced; and benzotrifluoride or its derivatives can be obtained in a good yield of 96% or higher in a single step.

Preferably, element chlorine is introduced into the reaction system, whereby lowering of the catalytic activity of aluminum fluoride is prevented, and the operation can be continued for a long period of time.

In the process of this invention, the starting material is benzotrichloride or its derivatives (hereinafter referred to as "benzotrichloride compound"). As the derivative of benzotrichloride, there may be used any compound having a chemical structure constituted with a benzene ring, and at least one trichloromethyl group and optionally one or more of substituents, which do not materially interfere the reaction between the trichloromethyl group and hydrogen fluoride, on the benzene ring. Examples of such substituents are lower alkyl (e.g. methyl, ethyl), nitro, amino, cyano, halogen (e.g. chlorine, bromine, iodine), etc. Thus, the term "benzotrichloride compound" includes those of the formula:

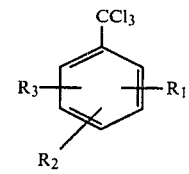

wherein $R_1$, $R_2$ and $R_3$ are each hydrogen, trichloromethyl, lower alkyl (e.g. methyl, ethyl), nitro, amino, cyano or halogen. Specific examples of the benzotrichloride compound are o-chloro-benzotrichloride, p-chloro-benzotrichloride, 2,4-dichloro-benzotrichloride, 2,4,6-trichloro-benzotrichloride, etc.

The molar ratio of hydrogen fluoride to the benzotrichloride compound is not limited. However, there is usually employed an equimolar or slight excess amount (not more than two molar amount) of hydrogen fluoride relative to the number of the chlorine atoms to be substituted in the benzotrichloride compound. When, for instance, the starting benzotrichloride compound is benzotrichloride, the number of the chlorine atoms to be substituted is 3, so that hydrogen fluoride is usually employed in an amount of about 3 to 6 moles to 1 mole of benzotrichloride.

The aluminum fluoride used as the catalyst in the process of the invention may be produced by any conventional procedure. There is no limitation on its crystalline form. In general, β-aluminum fluoride or γ-aluminum fluoride, or their mixture is favorably used.

The reaction temperature in the process of the invention may be usually from about 200° to 450° C., preferably from about 250° to 350° C. A temperature below 200° C. or above 450° C. is not practical because of the low reaction rate in the former and of the severe deterioration of the catalyst in the latter. The pressure is not limited and may be below or above atmospheric pressure; it is preferred to be from 1 to 3 absolute pressures.

The contact time depends upon the reaction temperature, the catalytic activity of the catalyst and the like. When, for instance, the aluminum fluoride prepared by treatment of activated alumina with hydrogen fluoride at a temperature of 200° to 500° C. as shown in Example 1 is employed as the catalyst, a space velocity of about 200 to 20000 hr$^{-1}$, particularly of about 500 to 10000 hr$^{-1}$, is preferred.

In carrying out the process of the present invention, designed amounts of the benzotrichloride compound, of hydrogen fluoride and, if desired, of chlorine may be charged, for instance, in a pre-heating apparatus and heated to make a gaseous mixture. The gaseous mixture is introduced into a tubular reactor packed with the catalyst, whereby the reaction proceeds at an elevated temperature. The reaction mixture discharged from the reactor is introduced into a distillation tower, and gaseous materials such as hydrogen chloride and hydrogen fluoride are taken out from the top of the tower while liquid materials including the produced benzotrifluoride or its derivatives are taken out from the bottom of the tower.

The reactor may be made of any material resistant to corrosion by hydrogen fluoride, hydrogen chloride, chlorine and the like at an elevated temperature. Examples of such material are stainless steel, nickel, nickel alloy (e.g. Inconel, Hastelloy), etc.

In the course of the process of this invention, for instance, about 10 hours after the initiation of the reaction, the lowering of the yield of the product or the deterioration of the catalytic activity of the catalyst is sometimes observed. Such deteriorated catalyst can be reactivated by contacting with elementary chlorine. The reactivated catalyst also can maintain its activity for a considerable period of time by continuing the contacting with elementary chlorine. On this ground, the introduction of elementary chlorine into the reaction system is favorable for prevention of the deterioration of the catalytic activity or reactivation of the once deteriorated catalyst. Such introduction may be effected during or after the reaction. Preferably, the introduction is carried out continuously or intermittently throughout or for a definite period of the reaction. For instance, chlorine may be mixed with the benzotrichloride compound and hydrogen fluoride and then introduced into the reactor charged with the catalyst. Further, for instance, chlorine may be introduced alone into the reactor packed with the catalyst, while the introduction of the benzotrichloride compound and hydrogen fluoride is ceased.

When chlorine is introduced into the reaction system while the reaction is continued, the amount of chlorine may be usually from about 0.5 to 10% by mole, preferably from 3 to 7% by mole relative to the benzotrichloride compound. A smaller amount of chlorine than the said lower limit is not sufficiently effective in recovery of the catalytic activity, and a larger amount than the said upper limit results in increase of the production of by-products.

When, due to the overuse, the recovery of the catalytic activity cannot be attained any more by contacting with chlorine, the deteriorated catalyst may be contacted with oxygen or air at a temperature of 400° to 500° C. so that the catalyst will be reactivated.

The thus obtained reaction mixture comprises benzotrifluoride or its derivatives (hereinafter referred to as "benzotrifluoride compound"), which corresponds to the starting benzotrichloride compound. The derivative of benzotrifluoride may be the one having a chemical structure constituted with a benzene ring and at least one trifluoromethyl group thereon. In addition to at least one trifluoromethyl group, one or more of substituents such as nitro, cyano, halogen and the like may be present on the benzene ring. Thus the term "benzotrifluoride compound" includes those of the formula:

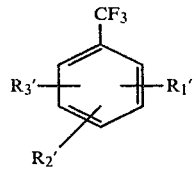

wherein $R_1'$, $R_2'$ and $R_3'$ are each hydrogen, trifluoromethyl, lower alkyl, nitro, amino, cyano or halogen.

Recovery of the benzotrifluoride compound from the reaction mixture may be carried out by a per se conventional separation procedure such as distillation.

The process of this invention is industrially advantageous in producing benzotrifluoride or its derivative efficiently in high yields without using any expensive reaction apparatus even under atmospheric pressure.

Practical and presently preferred embodiments of the invention are illustratively shown in the following Examples wherein the yield represents, unless otherwise indicated, a molar percentage of the benzotrifluoride compound to the benzotrichloride compound, i.e. the product of the conversion and the selectivity.

EXAMPLE 1

A "Hastelloy C" made tubular reactor (¾ inch in diameter) was charged with 50 g of granules of activated alumina having a size of 4 to 6 mm in diameter and heated to 200° C. in a stream of nitrogen. Thereafter, hydrogen fluoride was introduced to the reactor at a flow rate of 200 ml/min. When the shift of a hot spot ceased, i.e. when 3.5 hours elapsed from the introduction of hydrogen fluoride, the reactor was heated to 350° C. and kept at this temperature for 3 hours, during which the introduction of hydrogen fluoride was continued. After cooling, the activated alumina was subjected to X ray analysis, whereby it was revealed that most of the activated alumina was converted to a mixture of $\beta$-AlF$_3$ and $\gamma$-AlF$_3$. The resulting product consisted of 88.5% by weight of AlF$_3$ and 11.5% by weight of Al$_2$O$_3$.

Fifty grams of the granular product as above obtained were charged into a "Hastelloy C" made tubular reactor (¾ inch in diameter). The reactor was heated and maintained at 310° C., and a mixed gas of hydrogen fluoride and benzotrichloride (molar ratio=4:1) was fed thereto at atmospheric pressure. The flow rate of benzotrichloride was 1 g/min. The reaction product coming out of the reactor was led to a condensor cooled with ice, where the by-produced hydrogen chloride and the non-reacted hydrogen fluoride were separated from the non-volatile liquid product. The non-volatile product containing acidic materials was washed with water and dried over anhydrous sodium sulfate. The overall yield of crude benzotrifluoride after the continuation of the reaction for 10 hours was 444 g.

Gas chromatographic determination of the crude product showed that the benzotrifluoride content was 96.2% by weight and most of the rest was monochlorodifluoromethylbenzene.

EXAMPLE 2 p-Chloro-benzotrifluoride was prepared as in Example 1 except that benzotrichloride was replaced by p-chloro-benzotrichloride. The reaction lasted for 7 hours gave 323 g of crude p-chloro-benzotrifluoride. Gas chromatographic determination of the crude product showed that the p-chloro-benzotrifluoride content was 96.3% by weight and most of the rest was p-chloro-monochlorodifluoro-methylbenzene.

EXAMPLE 3

Benzotrifluoride was prepared as in Example 1 except that the reaction ran for 30 hours and that 5% by mol of chlorine relative to benzotrichloride was introduced into the reactor during the 11th to 14th hour and during the 26th to 29th hour from the initiation of the reaction. The yield of benzotrifluoride was 97% by mole at the beginning but gradually lowered and after 10 hours, was 95% by mole. The yield, however, was recovered to 97% by mole by introducing chlorine and kept constant by continuous introduction. The yield began to decrease again somewhat rapidly when the introduction of chlorine was interrupted after 15 hours from the initiation of the reaction and it was lowered to 70% by mole after 25 hours. Thereafter, the yield was recovered to 91% by mole by the introduction of chlorine, continued to increase and after 30 hours, was 95% by mole. The yields of benzotrifluoride at various reaction times are shown by the solid line in FIG. 1 of the accompanying drawing wherein the axis of abscissa indicates the reaction time (hr) and the axis of ordinate represents the yield of benzotrifluoride (mole %).

EXAMPLE 4

Benzotrifluoride was prepared as in Example 1 except that the reaction ran for 170 hours and that 5% by mole of chlorine relative to benzotrichloride was introduced into the reactor throughout the reaction. The yield of benzotrifluoride remained 97% by mole as shown by the dotted line in FIG. 1.

EXAMPLE 5 p-Chloro-benzotrifluoride was prepared as in Example 2 except that the reaction ran for 150 hours and that 4% by mole of chlorine relative to p-chloro-benzotrichloride was introduced into the reactor throughout the reaction. The yield of p-chloro-benzotrifluoride remained 97.2% by mole.

What is claimed is:

1. A process for preparing benzotrifluoride or its derivative by contacting benzotrichloride or its derivative corresponding thereto with hydrogen fluoride in a gaseous phase, characterized in that the contact is carried out in the presence of aluminum fluoride.

2. The process according to claim 1, wherein hydrogen fluoride is used in an amount of about 1 to 2 moles to each chlorine atom to be substituted in benzotrichloride or its derivative.

3. The process according to claim 1, wherein the aluminum chloride is of $\beta$- or $\gamma$-type or a mixture thereof.

4. The process according to claim 1, wherein the contacting is effected at a temperature of 200° to 450° C.

5. The process according to any of claims 1 to 4, wherein the contacting is effected in the presence of elementary chlorine.

6. The process according to claim 5, wherein the elementary chlorine is used in an amount of about 0.5 to 10% by moles to benzotrichloride or its derivative.

7. In the preparation of benzotrifluoride by a process which comprises catalytically reacting benzotrichloride with hydrogen fluoride, the improvement which comprises reacting in the gaseous phase benzotrichloride and hydrogen fluoride in the presence of an aluminum fluoride catalyst thereby producing benzotrifluoride at an accelerated rate and avoiding vigorous agitation of a liquid medium containing hydrogen fluoride at high pressures and high temperatures.

* * * * *